United States Patent
Kuriyama et al.

(10) Patent No.: US 7,310,406 B2
(45) Date of Patent: Dec. 18, 2007

(54) INSPECTION METHOD AND SYSTEM FOR AND METHOD OF PRODUCING COMPONENT MOUNTING SUBSTRATE

(75) Inventors: Jun Kuriyama, Fukuchiyama (JP); Masato Ishiba, Kyoto (JP); Kiyoshi Murakami, Kyoto (JP); Teruhisa Yotsuya, Kyoto (JP)

(73) Assignee: OMRON Corporation, Kyoto (JP)

( * ) Notice: Subject to any disclaimer, the term of this patent is extended or adjusted under 35 U.S.C. 154(b) by 0 days.

(21) Appl. No.: 11/168,015

(22) Filed: Jun. 27, 2005

(65) Prior Publication Data

US 2006/0002510 A1   Jan. 5, 2006

(30) Foreign Application Priority Data

Jun. 30, 2004 (JP) ............................. 2004-193601
Jun. 24, 2005 (JP) ............................. 2005-184416

(51) Int. Cl.
*G01N 23/04* (2006.01)
*G01N 21/88* (2006.01)
*G01N 21/956* (2006.01)

(52) U.S. Cl. ................... 378/57; 378/98.12; 250/559.4
(58) Field of Classification Search ................ 378/41, 378/51, 62, 70, 98.12, 58, 20, 57, 210; 250/358.1, 250/359.1, 360.1, 559.4, 559.34, 559.36, 250/559.39; 382/150
See application file for complete search history.

(56) References Cited

U.S. PATENT DOCUMENTS

| | | | | |
|---|---|---|---|---|
| 3,573,455 | A * | 4/1971 | Suierveld | 378/58 |
| 5,097,492 | A * | 3/1992 | Baker et al. | 378/22 |
| 5,182,775 | A * | 1/1993 | Matsui et al. | 382/152 |
| 5,493,594 | A * | 2/1996 | Hamada et al. | 378/34 |
| 6,185,273 | B1 * | 2/2001 | Sperschneider | 378/58 |
| 6,573,523 | B1 * | 6/2003 | Long | 250/559.4 |
| 6,721,461 | B1 * | 4/2004 | Nichani | 382/270 |

(Continued)

FOREIGN PATENT DOCUMENTS

EP    0776151 A1    5/1997

(Continued)

OTHER PUBLICATIONS

Hanke, R.F., *Automated 3D X-Ray Inspection Of Fine Pitch PCB's*, 1992 IEEE/CHMT Int'l Electronics manufacturing Technology Symposium, Sep. 28, 1992, pp. 187-190.

(Continued)

*Primary Examiner*—Edward Glick
*Assistant Examiner*—Anastasia S. Midkiff
(74) *Attorney, Agent, or Firm*—Beyer Weaver LLP

(57) ABSTRACT

On a production line for component mounting substrate, mutually communicating inspection apparatus are each provided to a different one of production processes that are carried out sequentially such as the solder printing, component mounting and soldering processes. Each inspection apparatus can generate an X-ray transmission image of the substrate. Each inspection apparatus on the downstream side inputs an image from another inspection apparatus on the upstream side and generates a differential image of the inputted image and an X-ray transmission image of the same substrate generated by itself after the production process associated with itself is carried out. The differential image thus generated is used for inspecting the substrate such that the effect of the associated production process can be more accurately inspected.

3 Claims, 8 Drawing Sheets

U.S. PATENT DOCUMENTS

2001/0040217 A1* 11/2001 Mizuoka et al. ......... 250/358.1
2001/0051304 A1* 12/2001 Stivers et al. .................. 430/5

FOREIGN PATENT DOCUMENTS

| JP | 03-072249 | 3/1991 |
| JP | 05-102698 | 4/1993 |
| JP | 05-108798 | 4/1993 |
| JP | 05-288538 | 11/1993 |
| JP | 11-198343 | 7/1999 |
| JP | 11-344449 | 12/1999 |
| JP | 2001-050730 | 2/2001 |
| JP | 2002-134998 | 5/2002 |
| JP | 2002-261500 | 9/2002 |
| WO | WO03/077291 A1 | 9/2003 |

OTHER PUBLICATIONS

European Search Report, patent application No. 05014084.7—2204 PCT, dated Oct. 17, 2005.
Japan patent application No. 2005-184416, Examination Report dated Feb. 27, 2007.

* cited by examiner

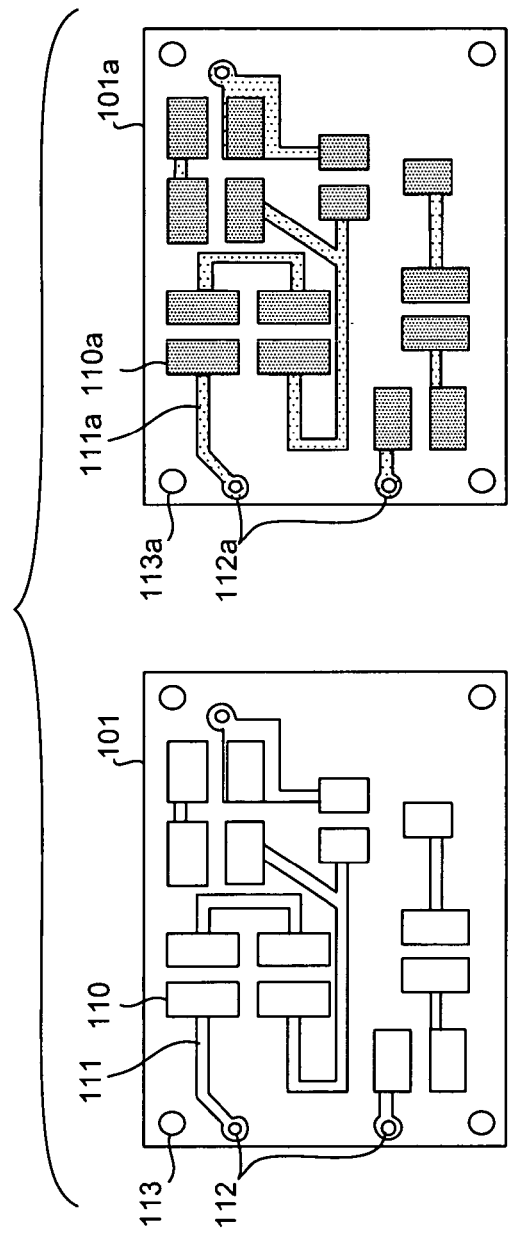
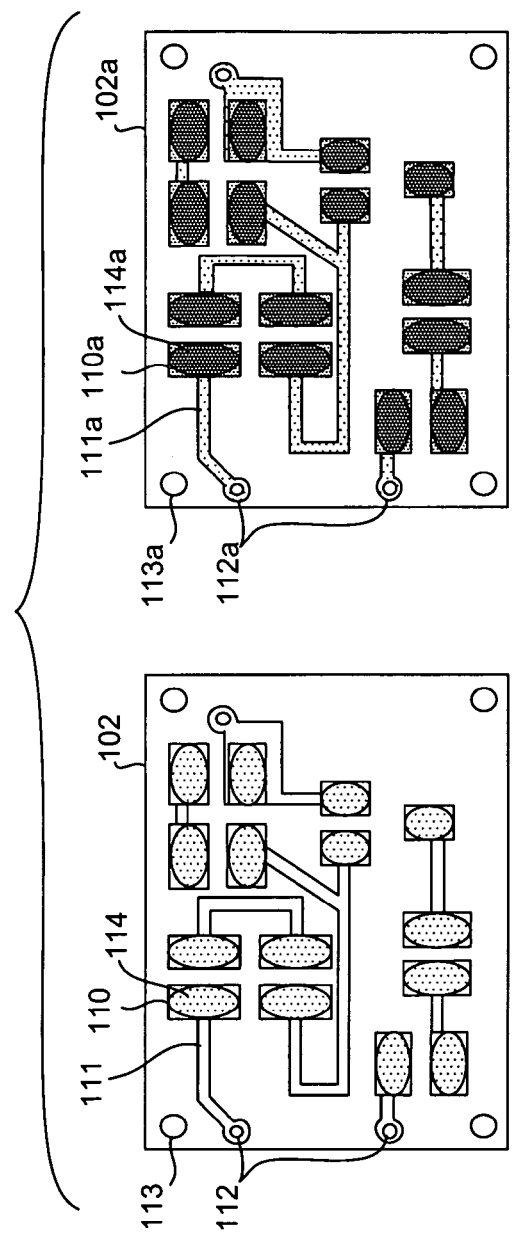

INSPECTION METHOD AND SYSTEM FOR AND METHOD OF PRODUCING COMPONENT MOUNTING SUBSTRATE

Priority is claimed on Japanese Patent Applications 2004-193601 filed Jun. 30, 2004 and 2005-184416 filed on Jun. 24, 2005.

BACKGROUND OF THE INVENTION

This invention relates to a substrate with components mounted thereon which has been completed or is still in its production process and more particularly to a method and a system for carrying out inspections by using X-ray transmission images thereon. The invention also relates to a method of producing such a component mounting substrate while carrying out such inspections in each of production processes that are carried out sequentially.

The general production process for component mounting substrates includes a solder printing process in which a printed circuit board is printed upon with cream solder, a component mounting process in which components are placed at positions where cream solder has been applied and a soldering process in which the substrate loaded with the components is heated for soldering. Along a production line for carrying out these processes sequentially, it is a common practice to carry out an inspection after each process such that substrates with a defect generated in that process will not be delivered to the next process.

It has been known to use an X-ray transmission image for an inspection of this type. Japanese Patent Publication Tokkai 6-237076, for example, disclosed an inspection apparatus for inspecting the soldered condition of a substrate by using an X-ray transmission image. Japanese Patent Publication Tokkai 2001-50730 relates to the production of a substrate with components mounted to both of its surfaces by obtaining a differential image showing the difference between its X-ray transmission image obtained when the mounting of components onto its one side has been completed and the image obtained after the mounting of components onto both sides has been completed and inspecting the solder condition on the second substrate surface.

On a component mounting substrate that has been completed, however, most of the solder is overlapping with lands and components are over the solder. It is difficult to make judgments on the conditions of individual components by separating them from such superposed portions. Inspection apparatus using laminography have been proposed in view of this problem but they are not easy to introduce for actual use because their structure is complicated and the production cost is adversely affected.

SUMMARY OF THE INVENTION

It is therefore an object of this invention in view of the above to use a relatively inexpensive apparatus for generating a simple X-ray transmission image to carry out an accurate inspection of results after each production process.

An inspection method of this invention is for a component mounting substrate being produced through a plurality of production processes carried out sequentially and may be characterized as comprising the steps of providing each of these production processes with an inspection apparatus provided with a device for generating an X-ray transmission image, and carrying out an inspection of the substrate after each of these production processes by using an X-ray transmission image (or an inspection image) generated by the image generating device of the associated one of the inspection apparatus. Each of the inspection apparatus, except for the inspection apparatus associated with the first of the production processes, inputs the X-ray transmission image generated by the inspection apparatus on the upstream side and inspects the substrate by using a differential image of the inputted image and the image generated by itself.

In the above, the production processes to be carried out sequentially may include combinations of two processes such as that of a production process for printed circuit boards and a solder printing process, that of a solder printing process and a component mounting process, and that of a component mounting process and a soldering process and a combination of three processes such as that of a solder printing process, a component mounting process and a soldering process. When component mounting substrates of a two-sided type are produced, the soldering process on one surface and the soldering process on the opposite surface may be considered as an example of a plurality of production processes to be carried out sequentially.

These sequentially performed processes need not be carried out such that the second process is started as soon as the first process is completed. A conveyor may be provided between two successively performed processes but such a setup is not required. These processes may be physically separated and apart.

The inspection apparatus according to this invention may preferably include an image processor in addition to a device for generating an X-ray transmission image inclusive of an X-ray generator and a camera. It is preferable that these inspection apparatus be set up such that communications are possible among them and generated X-ray transmission images can be inputted and outputted among them. Transfers of X-ray transmission images need not be through a communication means but may also be through the use of a memory medium such as a CD-R or an MO disk.

The device for generating an X-ray transmission image (or an inspection image) is preferably of a kind for generating an image having logarithmically converting the quantity of transmitted X-rays. This is because the quantity of transmitted X-rays can be expressed as an exponential function and if a logarithmically converted image is generated by each inspection apparatus, a difference between quantities of transmitted X-rays can be easily extracted by a differentiation process. It is preferable to use a logarithmic conversion camera for generating such an image but a similar image can be obtained by using an ordinary camera by taking images by changing the exposure time in a stepwise fashion.

It is also preferable to adjust the quantity of X-ray projection and the gain of the image at each inspection apparatus such that the image density for a single sample will be constant among the inspection apparatus.

According to the method of this invention, an X-ray transmission image of the substrate is generated after each production process has been carried out for an inspection by image processing. Each of the inspection apparatus except for the one associated with the first of the production processes is adapted to input the X-ray transmission image of the same substrate generated by the inspection apparatus on the upstream side (associated with the immediately previous production process) and to carry out its inspection process by using the differential image of (or the image representing the difference between) this inputted image and the X-ray transmission image generated by itself. Thus, it is possible to isolate an image of the change due to the effect of the production process with which the inspection apparatus is associated. In other words, each of these inspection apparatus can inspect only the effect of the associated production process by excluding the effects of the earlier production processes (on the upstream side).

It is therefore preferable that each of these inspection apparatus be provided with means for inputting the ID data on the substrates such that the image of the target substrate for inspection will be taken in from another inspection apparatus without an error. Such ID data may be set as code data with a specified number of digits. Such ID data may be inputted by using a keyboard at the start of the inspection. If the ID data are affixed to the substrate in a visibly recognizable form such as a bar code or a two-dimensional code, it is preferable to provide a means for automatically reading off such ID code.

If such input means are provided, the inspection apparatus on the upstream side may be adapted to accumulate the X-ray transmission images generated by itself by correlating them with the ID data of the substrates such that a request for transmission of a required image can be transmitted from an inspection apparatus on the downstream side on the basis of such ID data. The inspection apparatus on the upstream side is not necessarily required to check the presence of any defect and may be adapted only to generate X-ray transmission images and to transmit a requested image to an inspection apparatus on the downstream side.

If the production processes are characterized as including a printed board production process and a solder printing process, the inspection apparatus associated with the solder printing process may be adapted to input an X-ray transmission image generated by the inspection apparatus associated with the printed board production process and to inspect printed condition of the substrate by using a differential image of the inputted X-ray transmission image and an X-ray transmission image generated by itself. If the production processes include a solder printing process and a component mounting process, the inspection apparatus associated with the component mounting process may be adapted to input an X-ray transmission image generated by the inspection apparatus associated with the solder printing process and to inspect component mounting condition of the substrate by using a differential image of the inputted X-ray transmission image and an X-ray transmission image generated by itself.

If the production processes include a component mounting process and a soldering process, the inspection apparatus associated with the soldering process may be adapted to input an X-ray transmission image generated by the inspection apparatus associated with the component mounting process and to inspect solder condition of the substrate after the soldering process by using a differential image of the inputted X-ray transmission image and an X-ray transmission image generated by itself. This is because the change in the distribution of solder thickness due to its melting can be extracted from such a differential image.

If the production processes include a solder printing process, a component mounting process and a soldering process, an X-ray transmission image of the substrate may be preliminarily generated prior to the solder printing process and the inspection apparatus associated with the solder printing process may be adapted to generate a differential image of the X-ray transmission image of the substrate prior to the solder printing process and the image of the substrate after the solder printing process and to inspect printed condition of the substrate by using this differential image. This image to be preliminarily generated may be generated after the printed circuit board has been produced and the result of this process to be inspected by the inspection apparatus associated with the solder printing process may be used for this purpose before the solder printing process takes place. A differential image can be generated and used for inspection also in the component mounting process and the soldering process by inputting an X-ray transmission image of the substrate from the inspection apparatus associated with the immediately previous production process.

When the production processes include a solder printing process, a component mounting process and a soldering process, they may be repeated twice on a single target substrate to produce a component mounting substrate of a two-sided type. For this purpose, the inspection apparatus associated with the solder printing process may be adapted, when inspecting the substrate after the second solder printing process is completed, to input an X-ray transmission image of the substrate generated by the inspection apparatus associated with the soldering process during the first solder printing process and to inspect printed condition of the substrate after the second soldering process by using the differential image of the inputted X-ray transmission image and the X-ray transmission image generated by itself.

When a component mounting substrate of a two-sided type is produced as explained above, an X-ray transmission image of the substrate may be preliminarily generated prior to the solder printing process and the inspection apparatus associated with the solder printing process may be adapted to generate a differential image of the X-ray transmission image of the substrate prior to the solder printing process and the image of the substrate after the solder printing process and to inspect printed condition of the substrate after the first solder printing process by using the differential image generated by itself.

This inspection method for a two-sided type of component mounting substrate is applicable to a production line including a production process for a printed circuit board, a solder printing process, a component mounting process and a soldering process. An inspection apparatus may be also provided to the process for producing the printed circuit board such that an X-ray transmission image therefrom can be inputted and used for the inspection process after the first solder printing process for the inspection of the substrate. When the back surface side of the substrate is processed, the solder printing process is carried out first.

The invention also relates to an inspection method which may be characterized as being for a component mounting substrate produced through a plurality of production processes including a solder printing process and as comprising the steps of providing an inspection apparatus having an image generating means for generating an X-ray transmission image associated with the solder printing process, preliminarily generating an X-ray transmission image of a substrate, thereafter carrying out the solder printing process on the substrate, thereafter using the image generating means to generate an X-ray transmission image of the substrate on which the solder printing process has been carried out, inputting the preliminarily generated X-ray transmission image to the inspection apparatus, and inspecting printed condition of the substrate by using a differential image of the inputted X-ray transmission image and the X-ray transmission image generated by the image generating means.

In this method, the X-ray transmission image of the printed circuit board (that is, the substrate before the solder printing process is effected thereon) may be generated by a device other than the device incorporated in the aforementioned inspection apparatus. When the printed circuit board is inspected, an X-ray transmission image generated by the inspection apparatus for this inspection may be used.

By using a differential image as explained above, effects of structures formed on the printed circuit board such as lands, resist patterns and throughholes can be ignored and an image of the changes effected in the solder printing process (namely the cream solder portion) can be extracted for an accurate inspection of the printed condition of the cream solder.

An inspection system of this invention is for a component mounting substrate being produced through a plurality of production processes carried out sequentially and may be characterized as comprising inspection apparatus each provided with a device for generating an X-ray transmission image and associated with a different one of production processes and image outputting means each associated with a different one of the inspection apparatus, except for the inspection apparatus associated with the last of the production processes, and adapted to output an X-ray transmission image of the component mounting substrate generated by the inspection apparatus associated therewith to the inspection apparatus associated with the next production process. Each of these inspection apparatus, except for the inspection apparatus associated with the first of the production processes, is provided with an image inputting means for inputting an X-ray transmission image of the component mounting substrate generated by and sent from another of the inspection apparatus, a differential image generating means for generating a differential image of the inputted X-ray transmission image and the X-ray transmission image generated by the inspection apparatus associated with itself, and an inspecting means for inspecting the component mounting substrate by using the generated differential image generated by the differential image generating means.

Each of these inspection apparatus may be provided with an image processing means and a communication means for communicating with the other inspection apparatus. The aforementioned image inputting and outputting means may communicate with the other inspection apparatus to input and output images. The communications may be through wires or wireless means. Only the means for generating X-ray transmission images and the image outputting means are required of the inspection apparatus associated with the first production process. The differential image generating means and the inspecting means are not necessarily required.

The differential image generating means and the inspecting means may be considered portions of the image processing means, and each may preferably be realized as a computer storing programs. It is also preferable that the differential image generating means be provided with functions of correcting positional displacements, differences in density and differences in magnification between two images and be adapted to carry out image differentiation processes after making these corrections.

According to a preferred embodiment, the plurality of production processes include a solder printing process, a component mounting process and a soldering process and the inspection apparatus associated with the solder printing process is adapted to use the image inputting means to input an X-ray transmission image of the component mounting substrate prior to going through the solder printing process and to carry out a process by the differential image generating means and the inspecting means uses the differential image generated by the differential image generating means to inspect the component mounting substrate. If a similar inspection apparatus is also provided to the process for the production of printed circuit board, this may also be made a part of the system of this invention. In such a case, the inspection apparatus associated with the solder printing process may be adapted to input an X-ray transmission image of the substrate before its solder printing process from the inspection apparatus associated with the production process of printed circuit board. If no inspection apparatus is associated with the production process of printed circuit board, it is preferable that the inspection apparatus associated with the solder printing process be adapted to generate a X-ray transmission image of the substrate both before and after the solder printing process.

According to another preferable embodiment, the plurality of production processes include a solder printing process, a component mounting process and a soldering process and the inspection system is adapted to carry out these production processes twice on a component mounting substrate of a two-sided kind. The inspection apparatus associated with the soldering process includes an image outputting means for outputting the X-ray transmission image generated after the first soldering process on the component mounting substrate to the inspection apparatus associated with the solder printing process. The inspection apparatus associated with the solder printing process is adapted to inspect the component mounting substrate after the first solder printing process by inputting the X-ray transmission image before the solder printing process and to inspect the component mounting substrate after the second solder printing process by inputting the X-ray transmission image generated by the inspection apparatus associated with the soldering process. Its inspecting means serves to inspect printed condition of the component mounting substrate by the solder printing process.

A method of this invention for producing a component mounting substrate is characterized as comprising the steps of subjecting a substrate sequentially to a plurality of production processes, providing mutually communicating inspection apparatus each associated with a different one of these production processes and each including an image generating means for generating an X-ray transmission image, and inspecting the substrate after each of the production processes by the inspection apparatus associated therewith by an X-ray transmission image of the substrate after the production process generated by the image generating means associated therewith. Each of the inspection apparatus except for the inspection apparatus associated with the first of the production processes is adapted to carry out an inspection of the substrate by inputting an X-ray transmission image received from the inspection apparatus on the upstream side and using a differential image of the inputted image and an X-ray transmission image generated by itself.

According to a preferable embodiment, the plurality of production processes include a solder printing process, a component mounting process and a soldering process. The inspection method further comprises the step of preliminarily generating an X-ray transmission image of the substrate prior to the solder printing process, and the inspection apparatus associated with the solder printing process is adapted to generate a differential image of the X-ray transmission image of the substrate prior to the solder printing process and the image of the substrate after the solder printing process and to inspect printed condition of the substrate by using the differential image.

According to this invention, after a specified production process is completed on a substrate, a differential image is obtained from an X-ray transmission image of the substrate before this process and another after this process and this differential image is used to carry out an inspection. Thus, only the structural characteristics added by this production process are inspected. Since an image to be inspected can be extracted easily, an accurate inspection becomes possible with an inspection apparatus with a relatively inexpensive structure.

BRIEF DESCRIPTION OF THE DRAWINGS

FIGS. 3A and 3B, referred to together as FIG. 3, are the view and the image of a target substrate for inspection respectively at the bare substrate inspecting apparatus and at the solder printing inspection apparatus.

DETAILED DESCRIPTION OF THE INVENTION

Figure 1:
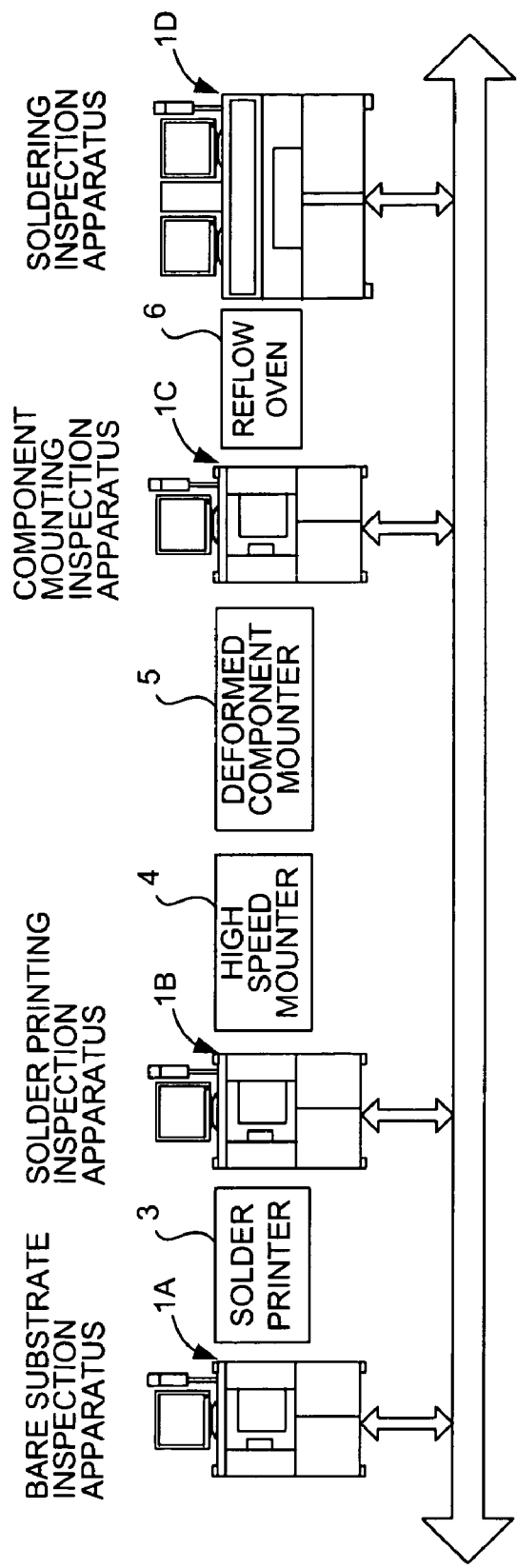
FIG. 1 is a diagram of an example of production line for substrates using the present invention.

FIG. 1 shows the structure of a production line for substrates using the present invention, including a plurality of inspection apparatus 1 besides various production apparatus such as a solder printer 3, a high-speed mounter 4, a deformed component mounter 5 and a reflow oven 6. One of a total of four inspection apparatus ("bare substrate inspecting apparatus" 1A) is disposed in front of the solder printer 3, another ("solder printing inspection apparatus" 1B) between the solder printer 3 and the high-speed mounter 4, a third ("component mounting inspection apparatus" 1C) between the deformed component mounter 5 and the reflow oven 6, and the fourth ("solder inspection apparatus" 1D) behind the reflow oven 6.

The inspection apparatus 1 are each adapted to carry out an inspection by means of an X-ray transmission image and are set up so as to be able to communicate one another through a network line 2 such as a LAN line. Conveyor devices for transporting substrates between these production and inspection apparatus arranged in the illustrated order are not shown in FIG. 1.

The solder printer 3 is adapted to have a printed circuit board supplied to it and to carry out a solder printing process whereby cream solder is applied to a soldering position of each component. The high-speed mounter 4 is for mounting chip components at a high rate. The deformed component mounter 5 is for mounting components other than chip components. The component mounting process is carried out by these two kinds of mounters 4 and 5. The reflow oven 6 is for carrying out the soldering process by heating the substrates after the component mounting process. The bare substrate inspecting apparatus 1A serves to inspect the conditions of lands, etc. on a bare substrate (that is, a printed circuit board before the solder printing on which resist patterns and lands are already formed) that is sent into this production line. The solder printing inspection apparatus 1B serves to inspect the correctness of the quantity of solder and positions of prints on a substrate after the solder printing process. The component mounting inspection apparatus 1C serves to inspect the presence or absence of component, positional displacements and appropriateness of directions of a substrate after the component mounting process. The solder inspection apparatus 1D serves to inspect the appropriateness of the distribution condition of solder after melting on a substrate after the soldering process.

Figure 2:
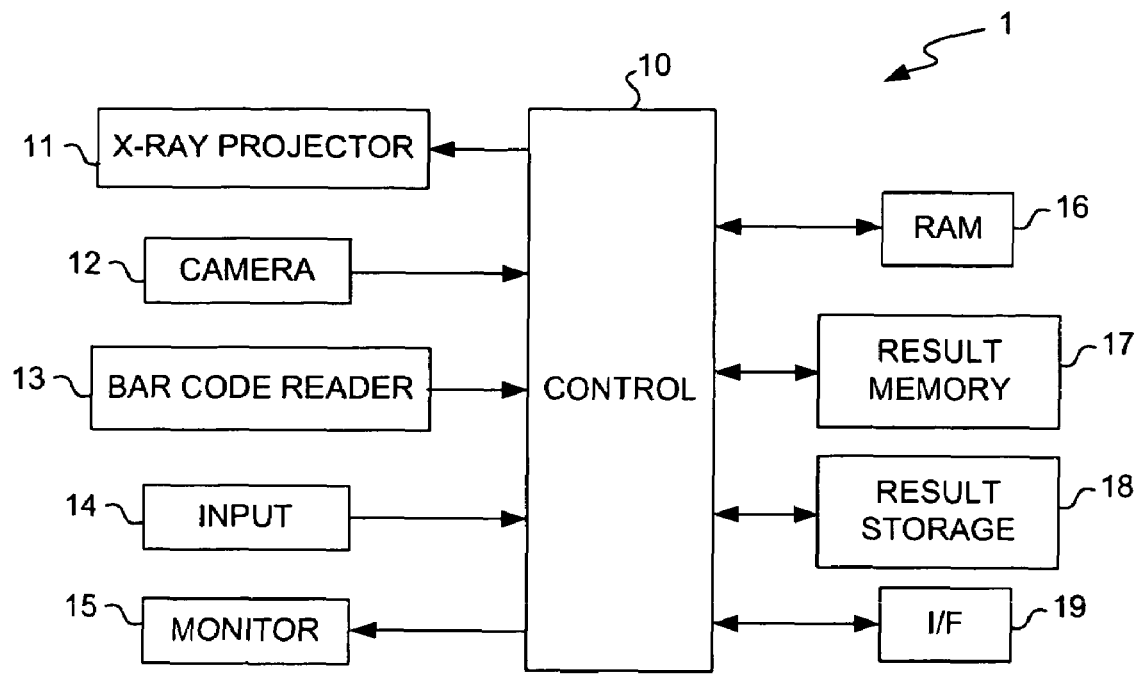
FIG. 2 is a block diagram of an inspection apparatus embodying this invention.

Each of these inspection apparatus 1 is provided with a substrate stage (not shown) for supporting a target substrate to be inspected and is adapted to carry out an inspection process by using an X-ray projector 11, a logarithmic conversion camera 12 (shown in FIG. 2) and a computer with an image processing capability. Set data for inspection areas, small areas (referred to as "windows") set for each target inspection position within the inspection area and standard values for measured data related to these inspection areas and windows are registered to each of these inspection apparatus 1 prior to the inspection. These data that are registered for the inspection are hereinafter referred to as inspection data.

Regarding the set data related to the inspection areas and windows, those common to all of these are inputted. According to the illustrated example, image generating processes are carried out preliminarily by all of the inspection apparatus 1 by using the same sample (such as a lead plate having a specified thickness) in order to adjust the quantity of radiation and the output gain of the camera 12 such that the image density corresponding to this sample will become equal.

According to this example, a single substrate sent through the production line is inspected by these inspection apparatus 1 sequentially. Each inspection apparatus 1 is arranged to carry out the inspection while communicating with the other inspection apparatus through the network line 2. In particular, the solder printing inspection apparatus 1B, the component mounting inspection apparatus 1C and the solder inspection apparatus 1D are each adapted to receive an X-ray transmission image of the substrate to be inspected by itself from the apparatus 1 on its upstream side and to carry out its own inspection by using both the received image and the image generated by itself.

In order to transmit and receive these images, a bar code label (not shown) having an ID code thereon is pasted on the substrate, and each inspection apparatus 1 is provided with a bar code reader 13 (shown in FIG. 2) for reading this bar code. At the time of an inspection, the bar code is read from the bar code label by means of the bar code reader 13 and an image requesting signal inclusive of this ID code is created and transmitted to the inspection apparatus 1 on the upstream side. The X-ray transmission image generated by itself is stored in the memory in correlation with the ID code of the corresponding substrate. When an image requesting signal is received from another inspection apparatus 1, the image corresponding to the ID code in this received signal is read out of the memory and transmitted to the inspection apparatus 1 which issued the request.

Each of these inspection apparatus 1 comprises a control part 10 formed by a computer which is connected not only to the X-ray projector 11, the logarithmic conversion camera (hereinafter simply referred to as the camera) 12 and the bar code reader 13 but also to an input part 14, a monitor 15, a work memory (RAM) 16, an inspection result memory 17, an inspection result storage part 18 and a communication interface 19. The control part 10 includes not only a CPU but also a ROM that stores basic programs. Although not shown in FIG. 1, an interface circuit for the input of images and an A/D converter circuit are disposed between the camera 12 and the control part 10.

The X-ray projector 11 and the camera 12 are disposed so as to sandwich the substrate stage therebetween. The bar code reader 13 is placed at a position above the substrate stage so as to be able to obtain and image of the bar code label. An X-ray transmission image generated by the camera 12 is converted by the A/D converter circuit and then stored in the work memory 16. Dedicated memory areas not only for the X-ray transmission image generated by itself but also for the image transmitted from the inspection apparatus 1 on the upstream side and the differential image to be explained below are set in the work memory 16.

The input part 14 comprises a keyboard and a mouse and is used for inputting the kind of the substrate at the start of the inspection and various set data at the time of a teaching process. The monitor 15 is used for the display of the user interface at the time of teaching, the target image to be inspected and the results of inspection.

The inspection result memory 17 is a memory for storing the aforementioned inspection data. The inspection data are in the form of files according to the kinds of substrate. As a substrate name is inputted from the input part 14 at the time of inspection, the inspection data file corresponding to this input is read out and set in the work memory 16. If there are some fluctuations in the substrate size among the images from the inspection apparatus 1, magnification of the image after correction with respect to the image at the present point of time may be obtained as parameter necessary for correcting the fluctuations but such magnification is also stored in the inspection result memory 17. The solder printing inspection apparatus 1B and the solder inspection apparatus 1D are adapted to preliminarily obtain the relationship between the thickness of solder and the density on the X-ray transmission image by calibration and to save a formula or a table that represents this relationship in the inspection result memory 17.

The inspection result storage part 18 is for the purpose of storing the inspection results and the X-ray transmission image of the substrate of which the inspection has been completed and is comprised of a hard disk device with a large capacity. According to the present example, a folder is set for each substrate with the ID code of this substrate used as the folder name and the image of the corresponding substrate and the inspection results are stored in this folder.

The communication interface 19 is for carrying out communications with the other inspection apparatus 1 through the network line 2.

With the structure as described above, as a target substrate to be inspected is transported in, the control part 10 uses the bar code reader 13 to read its ID code and then drives the X-ray projector 11 and the camera 12 to generate an X-ray transmission image of this target substrate. The image thus obtained is hereinafter also referred to as the inspection image. FIGS. 3 and 4 show in correlation external views 101, 102, 103 and 104 of a target substrate which is passed through the inspection apparatus 1 and its images 101a, 102a, 103a and 104a respectively generated by the inspection apparatus 1A, 1B, 1C and 1D.

At the bare substrate inspecting apparatus 1A, as shown in FIG. 3A, the target substrate 101 has lands 110, resist patterns 111, throughholes 112, position marks 113, etc. formed thereon and its image 101a obtained there includes images 110a, 111a, 112a and 113a respectively corresponding thereto. The bare substrate inspecting apparatus 1A extracts the image 110a of the lands and inspects appropriateness of their positions, sizes and orientations. This is done by setting a window (hereinafter referred to as the land window) for each land.

FIG. 3B shows the view of the target substrate 102 at the solder printing inspection apparatus 1B after the solder printing process and its image 102a. At this point in time, the target substrate 102 has solder 114 applied on the lands 110 such that the image 102a of the substrate shows the images 110a of the lands and the images 114a of the solder portions superposed.

Figure 4A:
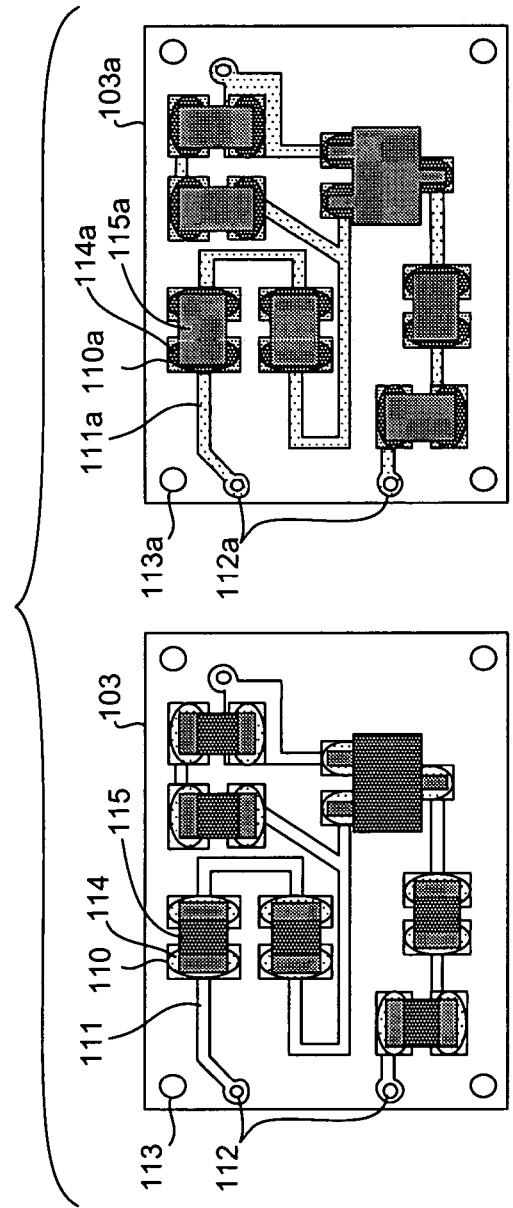
FIGS. 4A and 4B, referred to together as FIG. 4, are the view and the image of a target substrate for inspection respectively at the component mounting inspection apparatus and at the solder inspection apparatus.

FIG. 4A shows the view of the target substrate 103 at the component mounting inspection apparatus 1C after components have been mounted. At this point in time, the target substrate 103 has components 115 placed between two lands 110 such that the images 110a of each of the lands, the images 114a of the solder portions and the images 115a of the mounted components are all superposed.

Figure 4B:
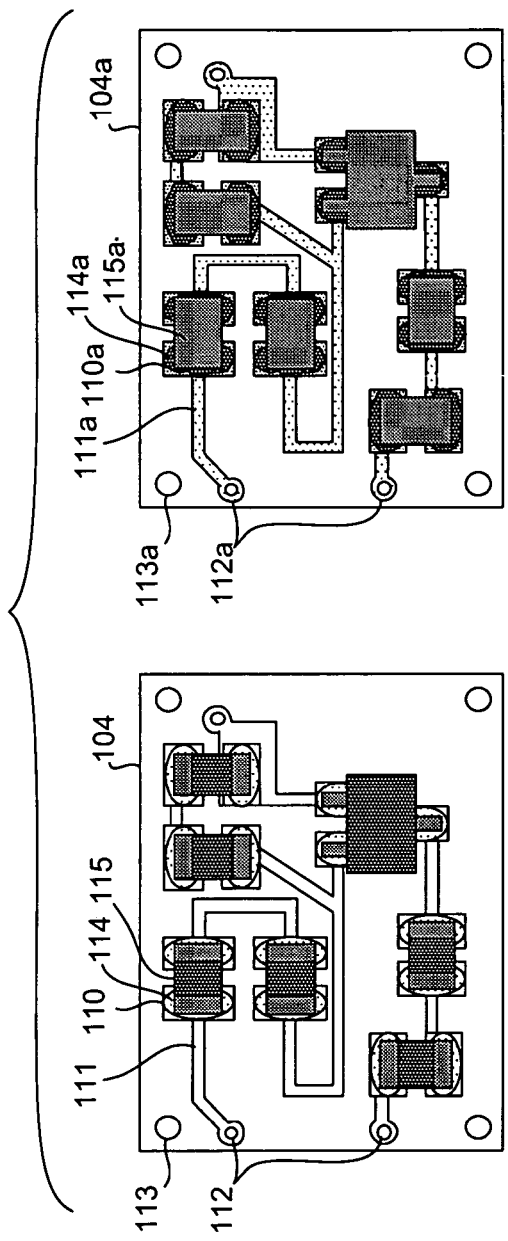

FIG. 4B shows the view of the target substrate 104 at the solder inspection apparatus 1D after the soldering process. The external view of the substrate is about the same between FIGS. 4A and 4B but the thickness of the solder changes due to the melting and the component may appear closer to the electrode. As a result, the image 104a shows a changed density distribution.

By this example, each of the four inspection apparatus 1 except the bare substrate inspection apparatus 1A receives the inspection image generated by the inspection apparatus 1A on the upstream side. This input process is carried out by the aforementioned communication using the image requesting signal. A differential image is generated from the received inspection image and the inspection image generated by itself in order to extract an image of the target inspection position and a required inspection is thereby carried out.

Because use is made of a logarithmic conversion camera for generating an inspection image according to this example, the difference in the quantity of transmitted X-rays between the images can be accurately extracted by a differentiation process. Where the solder 114 is above the land 110 and one target inspection position is superposed over another target position, in particular, a difference is obtained between images before and after the superposition and hence an image well reflecting the difference in the quantity of transmitted X-rays caused by the inspection target can be obtained. Thus, the position and the shape of the target of inspection can be accurately measured without the effects of other inspection targets on the back side.

Figure 5:
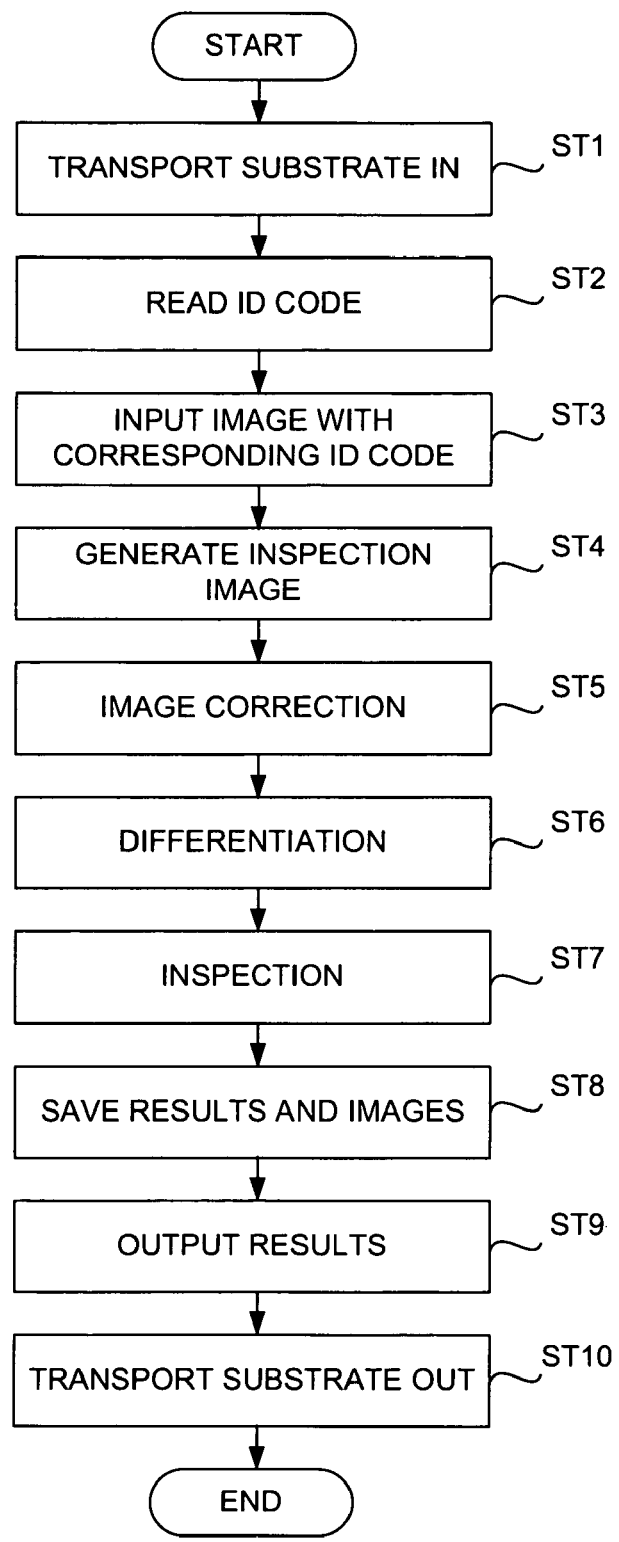
FIG. 5 is a flowchart of a routine carried out in common by the solder printing, component mounting and solder inspection apparatus.

Details of the inspection are explained next. Routines carried out in common by the inspection apparatus 1B, 1C and 1D on a substrate transported from the upstream side will be explained first with reference to the flowchart of FIG. 5.

After the transported substrate is placed on the substrate stage (Step ST1), the bar code reader 13 is used to read the ID code of the substrate (Step ST2). Next, an image requesting signal inclusive of the ID code that has been read out is transmitted to the inspection apparatus 1 on the upstream side (Step ST3). As the inspection apparatus 1 on the upstream side responds by reading out the inspection image corresponding to this image requesting signal from the inspection result storage part 18 and returns it, this returned image is stored in the work memory 16.

Next, the X-ray projector 11 and the camera 12 are driven to generate an inspection image by its own inspection apparatus 1 and the generated inspection image is also stored in the work memory 16 (Step ST4). Next, positional displacements between the inspection image generated in Step ST4 and the inspection image received in Step ST3 and the difference in size between them are corrected (Step ST5). In the above, the position displacements include not only displacements along a horizontal direction (x-direction) and a perpendicular direction (y-direction) but also a rotational displacement. The magnitudes of these displacements can be extracted by a correlation calculation between the images or by a matching process by using edge codes to be explained below about the component mounting inspection. The aforementioned magnification may be used as a parameter for the correction of the size difference between the images. The correction of an image can be effected by the affin conversion.

After this image correction process is completed, the difference between image data is obtained from each of corresponding pixels of the corrected inspection images and a differential image by these differential data of these individual pixels is generated and stored in the work memory 16 (Step ST6).

Next, an inspection process is carried out by using the differential image thus generated (Step ST7). The results of this inspection process and the inspection image generated in Step ST4 are stored in the inspection result storage part 18 in correlation with the ID code read out in Step ST2 (Step ST8). After the inspection results are outputted (Step ST9), the target substrate of inspection is transported out (Step ST10) to complete the routine.

Details of the inspection carried out in Step ST7 will be explained next for each of the inspection apparatus 1.

Figure 6:
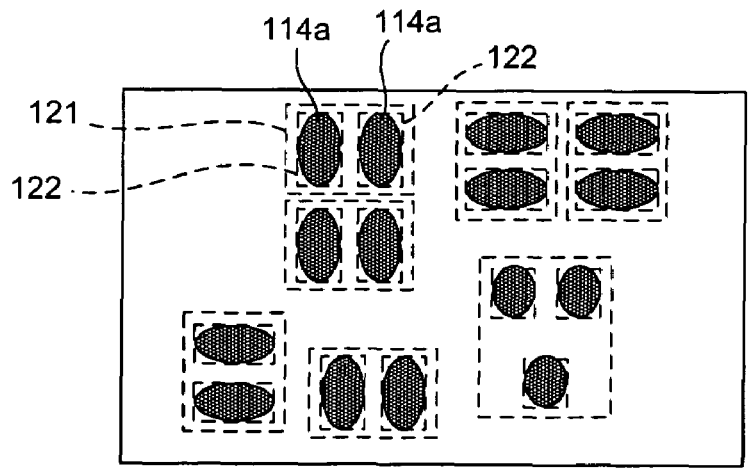
FIG. 6 is an example of differential image generated by the solder printing inspection apparatus.

FIG. 6 shows an example of differential image used by the solder printing inspection apparatus 1B for inspection. This is a differential image generated between the inspection image 101a inputted from the bare substrate inspection apparatus 1A and the inspection image 102a generated by the solder printing inspection apparatus 1B itself. The structures such as lands and resist patterns that are common between the images have disappeared and only the images 114a of the solder portions newly added in the solder printing process remain. In FIG. 6, numeral 121 indicates an individual inspection area for each component. Numerals 122 each indicate a land window set individually for each land.

Figure 7:
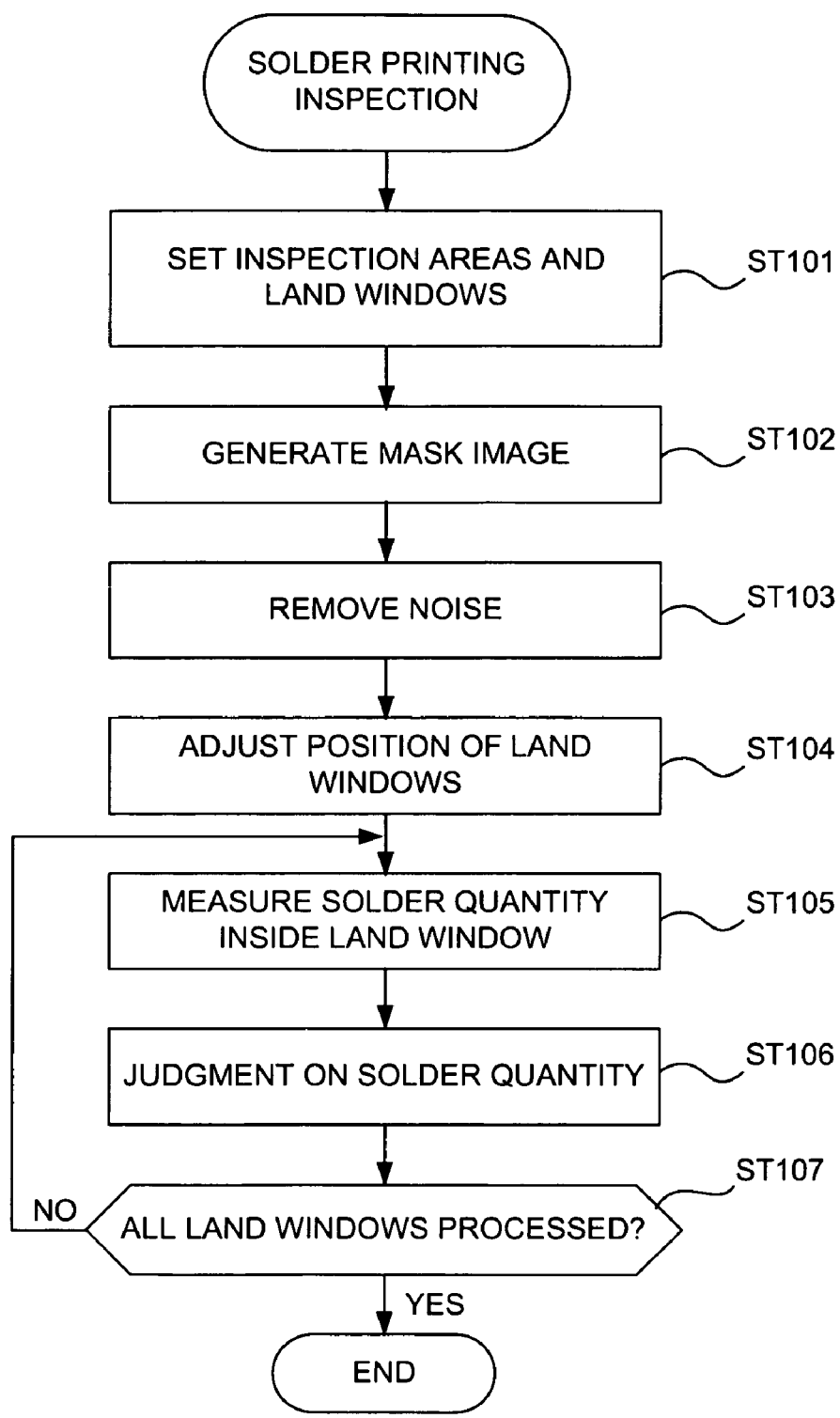
FIG. 7 is a flowchart of a routine for solder printing inspection.
Figure 8:
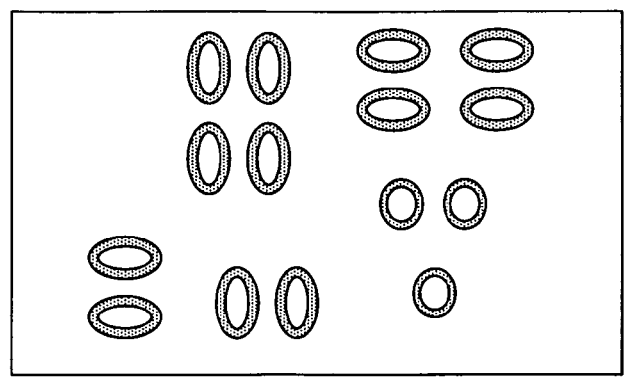
FIG. 8 is an example of mask image for removing noise.

FIG. 7 is a flowchart of the inspection routine carried out by the solder printing inspection apparatus 1B. In this routine, aforementioned inspection areas 121 and land windows are initially set up (Step ST101). Next, a so-called edge-extraction process is carried out for each land window 122 of the differential image. The extracted edges are expanded by a few pixels, and a mask image is created as shown in FIG. 8 by multiplying a gain or adding a specified offset value to the expanded portion (Step 102). The mask image thus created and the original differential image are compared at each pixel. On the differential image, if density at a certain pixel is less than that at the corresponding pixel on the mask image, this density is replaced by zero, while the density at other pixels is kept unchanged (Step S103). By this process, if there is a portion near the edge of the solder with density about equal to that on the image of a land, such portion can be eliminated as noise.

Steps S102 and ST103 are for the purpose of removing noise generated on the differential image. By the present example, as explained above, a same sample is used preliminarily to make adjustments such that the images generated by the inspection apparatus will have about the same density and positional displacements and magnifications are corrected before the differentiation process is carried out but there is a possibility that there still remain small differences in density and size among the images. Such differences may appear as noise on the differential image. If noise due to positional displacements appears near the edge of the image 114a of solder, in particular, the measured amount of the solder becomes erroneous. This is why a process such as Steps S102 and ST103 is necessary.

After the process for removing noise is completed, positional displacements of land windows 122 are corrected with respect to the image of solder after the removal of noise (Step ST104). Prior to this adjustment of positional displacement of land windows 122, however, the image 114a of solder may be expanded somewhat so as to recover the area reduced by the process for removing noise.

Thereafter, one of the land windows 122 is considered, and the data obtained by calibration are used to replace the density at each of the pixels in that land window 122 by the thickness of the solder and to carry out an integration calculation over the thickness of all pixels in the land window 122. The integrated value thus obtained is treated as representing the quantity of solder (Step ST105) and is compared with preliminarily registered standard data value to judge appropriateness of the quantity of solder (Step ST106). Steps S105 and S106 are repeated over all of the land windows, that is, until the judgment in Step ST107 becomes YES and the routine ends.

Figure 9:
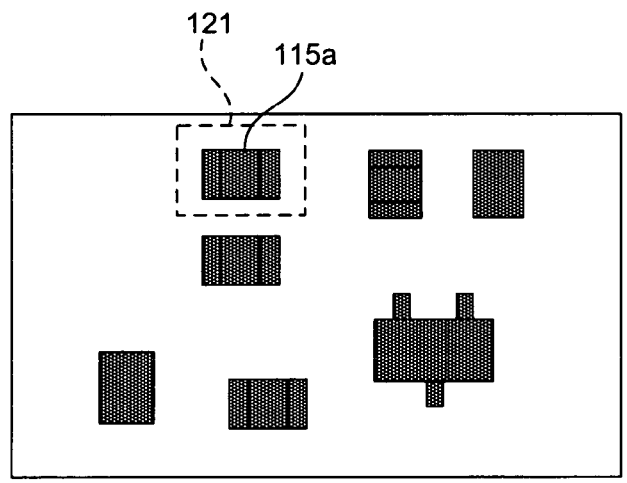
FIG. 9 is an example of differential image generated by the component mounting inspection apparatus.

FIG. 9 shows an example of differential image used by the component mounting inspection apparatus 1C for inspection. This is a differential image generated between the inspection image 102a inputted from the solder printing inspection apparatus 1B and the inspection image 103a generated by the component mounting inspection apparatus 1C itself. The structures that are common between the images have disappeared and only the images 115a of the components newly added in the component mounting process remain. In FIG. 9, too, individual inspection areas 121 are set under similar conditions.

Figure 10:
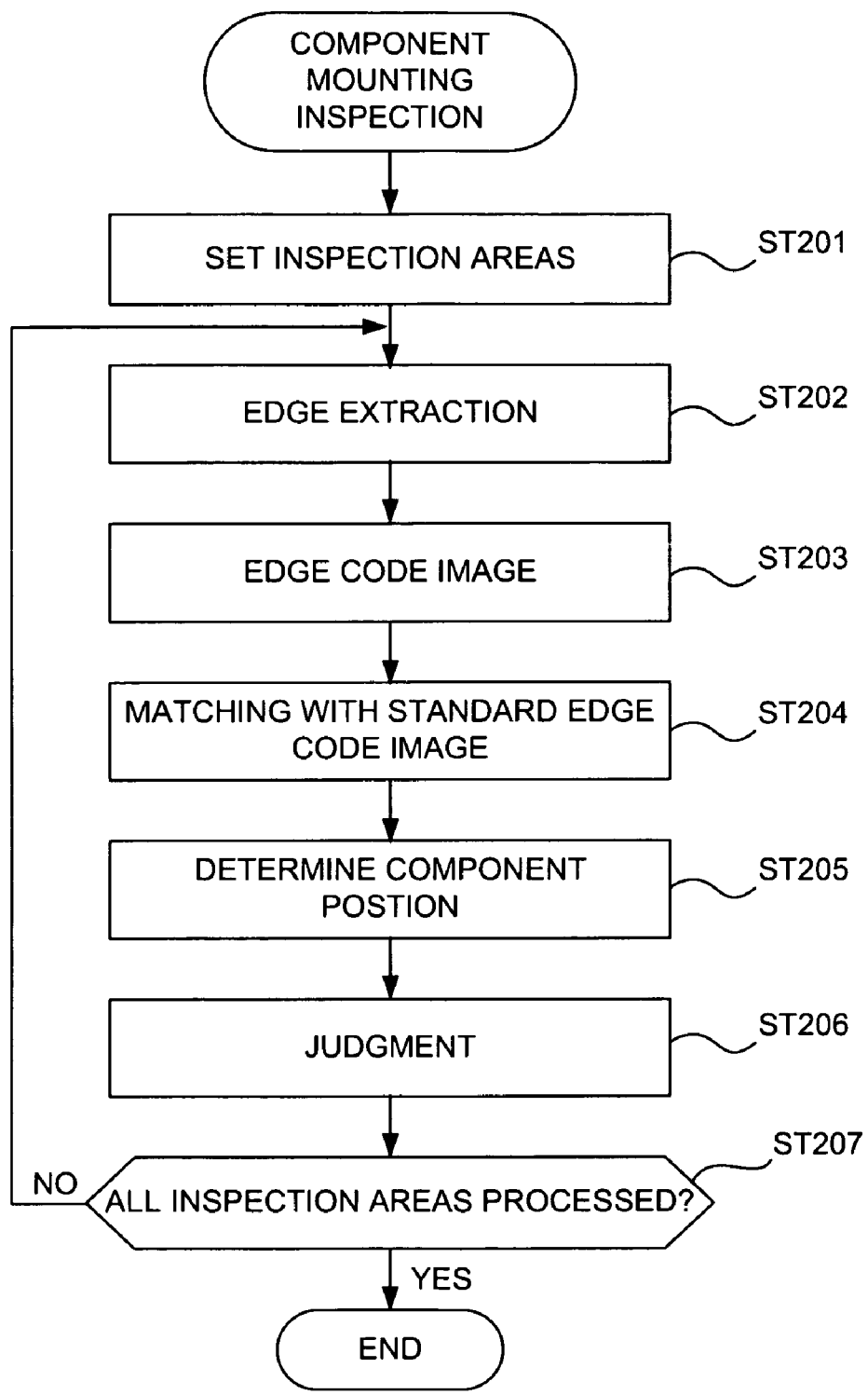
FIG. 10 is a flowchart of a routine for component mounting inspection.

FIG. 10 is a flowchart of the inspection routine carried out by the component mounting inspection apparatus 1C. In this routine, inspection areas 121 are initially set up similarly for the individual components on the differential image (Step ST201), and Steps ST202-ST206 to be described below are repeated next in each of these inspection areas 121.

In Step ST202, the aforementioned edge extraction process is carried out in the inspection area 121. In Step ST203, a virtual image (hereinafter referred to as edge code image) is generated by replacing the image data of each pixel in the inspection area 121 by the edge code. In the above, the edge codes are angle data indicative of the direction in which the density gradient changes with respect to the edge pixel, as explained in detail in Japanese Patent Publication Tokkai 2002-203233. According to the present example, edge codes are calculated only for edge pixels extracted by the edge extraction process in Step ST202, while the edge codes for other pixels are set equal to 0.

In Step ST204, a matching process is carried out on the edge code image generated in Step ST203 by using a standard edge code image. The standard edge code image is an image generated by preliminarily extracting an image of a component from the differential image of X-ray transmission images before and after components are mounted to a model substrate by also setting the edge code equal to zero for pixels other than edge pixels. In Step ST204, while the standard edge code image is scanned over the target edge code image to be processed, the difference between the edge codes is obtained for each pixel between the corresponding pixels at each scan position, and the sum of all these differences is obtained. After the scan, the position where the sum of differences between the edge codes is the smallest is identified as the position of the component (Step ST205).

It is thereafter determined whether the component is positioned correctly or not by comparing the coordinates of the position identified in Step ST205 with the standard coordinates (Step ST206). If the aforementioned sum of the differences is larger than a specified threshold value, however, it is determined that the component is not positioned correctly by concluding that the orientation of the component is not correct. Although not shown in the flowchart, if the number of extracted edge pixels is less than a specified value, the processes of Steps ST203-ST205 are skipped and it is concluded in Step ST206 that the component is missing.

Steps ST202-ST206 are repeated for each inspection area 121. The routine of FIG. 10 ends when it is determined that the processes have been completed for all of the inspection areas 121 (YES in Step ST207).

FIG. 9 shows an example of differential image used by the component mounting inspection apparatus 1C for inspection. This is a differential image generated between the inspection image 102a inputted from the solder printing inspection apparatus 1B and the inspection image 103a generated by the component mounting inspection apparatus 1C itself. The structures that are common between the images have disappeared and only the images 115a of the components newly added in the component mounting process remain. In FIG. 9, too, individual inspection areas 121 are set under similar conditions.

Figure 11:
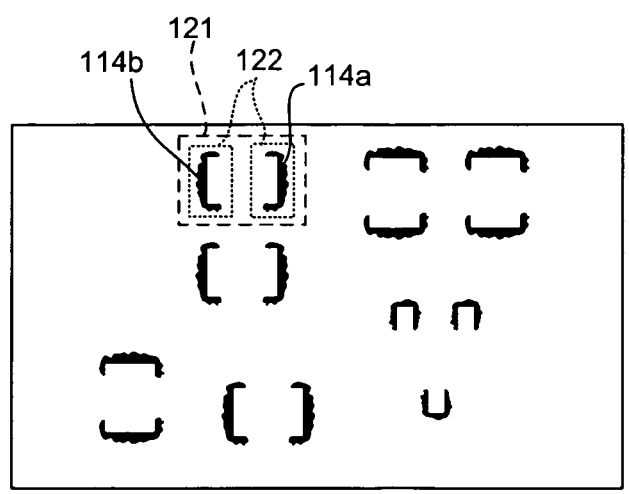
FIG. 11 is an example of differential image generated by the soldering inspection apparatus.

FIG. 11 shows an example of differential image used by the solder inspection apparatus 1D for inspection. This is a differential image generated between the inspection image 103a inputted from the component mounting inspection apparatus 1C and the inspection image 104a generated by the solder inspection apparatus 1D itself. Fixed structures such as components and lands have disappeared and only the images 114b reflecting the changes in the thickness of solder are extracted. As explained above, melted solder tends to move in the direction of the side of the component with electrodes because of its surface tension. Thus, the extracted images 114b form patterns extending near the electrode parts of the components.

The solder inspection apparatus 1D sets up land windows 122 on the differential image as done by the solder printing inspection apparatus 1B and extracts the thickness of solder at each pixel within the land windows 122. A standard pattern registering the standard thickness distribution of solder inside each land window is used for comparison and for determining whether the solder condition is appropriate or not.

In summary, each of the solder printing, component mounting and solder inspection apparatus 1B, 1C and 1D is adapted to generate a differential image for inspecting image generated by and received from the inspection apparatus 1 on the upstream side and the inspection image generated by itself and hence can accurately extract an image of the portion to be inspected.

The bare substrate inspection apparatus 1A on the extreme upstream side cannot carry out inspection by using any image generated by the other inspection apparatus 1B, 1C and 1D on the downstream side but is adapted to carry out an inspection by making use of the CAD data of the substrate, that is, by generating theoretical data of X-ray transmission image from patterns of lands and resists shown by the CAD data and the quantity of transmitted X-rays through the structure and measuring the difference between the theoretical data thus obtained and the inspection image actually generated. The area of a difference portion may be extracted from a differential image and a judgment may be made based on whether or not the area thus extracted is greater than a specified standard value.

The production line shown in FIG. 1 may be used for the production of substrates with components mounted on both surfaces. In this case, the production and inspection processes explained above with reference to FIG. 1 are sequentially on one surface of each substrate and then the substrate is turned upside down before the next sequence of processes is started. In this case, the bare substrate inspection apparatus 1A will not carry out the inspection for the second time and the substrate will be passed by it. At the time of the second inspection, the solder printing inspection apparatus 1B will input an inspection image from the solder inspection apparatus 1D and, after rotating the inspection image inputted from the solder inspection apparatus 1D by 180°, carry out the aforementioned image correction and differentiation processes by using this rotated image and the inspection image generated by itself.

The inspection image generated by the solder printing inspection apparatus 1B at the time of the second inspection will show not only the structure of the upper surface which is currently being inspected but also the structure of the lower surface which was earlier inspected. The image of the solder on the upper surface side can be extracted, however, by a differentiation process with the inspection image after the completion of inspection of the lower surface side. Thus, the condition of solder printing on both surface sides can be accurately inspected.

By contrast, the component mounting inspection apparatus 1C and the solder inspection apparatus 1D are both adapted to input an inspection image from the inspection apparatus 1 on the upstream side also at the time of the second inspection. It goes without saying that what they receive is the inspection image generated also at the time of the inspection of the second surface and hence the data on the structure (component) which has just been added or the change (of solder) immediately before the inspection about to be carried out can be extracted by differentiation. Thus, an accurate inspection can be carried out on both surfaces.

What is claimed is:

1. An inspection method for carrying out an inspection associated with a solder printing process, said solder printing process being one of a plurality of production processes carried out for producing component mounting substrates, said inspection method comprising the steps of:

providing said solder printing process with an inspection apparatus having an image generating device for generating X-ray transmission images;

receiving a substrate after said solder printing process and generating an X-ray transmission image of said substrate by said image generating device;

inputting an earlier obtained X-ray transmission image of said substrate generated before said solder printing process was carried out on said substrate;

using a differential image of said generated X-ray transmission image and said earlier obtained X-ray transmission image to inspect printed condition of said substrate; and registering setting data that are necessary for setting an inspection window to an area corresponding to each of lands in said differential image, conversion data necessary for converting density on said differential image to a value indicative of thickness of solder and a reference solder quantity at each inspection window before an inspection is carried out;

wherein said inspection includes:

first step of setting a plurality of inspection windows to said differential image by using said setting data;

second step of extracting edges in each of said inspection windows;

third step of expanding said edges extracted in said second step and creating a mask image that sets density corresponding to an X-ray transmission image of a land at an expanded portion;

fourth step of comparing said mask image with said differential image for each pixel and thereby obtaining a corrected differential image by correcting said differential image by replacing by zero the density of those of the pixels lower than that of corresponding pixel in said mask image and keeping unchanged the density of those of the pixels higher than that of corresponding pixel in said mask image;

fifth step of converting the density of each pixel in each of said inspection windows of said corrected differential image, based on said registered conversion data, into a value indicative of thickness of solder and obtaining an integrated value as representing solder quantity; and sixth step of comparing said solder quantity obtained in said fifth step with said registered reference solder quantity for each of said inspection windows and thereby judging whether the quantity of solder printed on each of said lands is proper or not.

2. The inspection method of claim 1 further comprising the steps of:

providing another inspection apparatus having an image generating device for generating X-ray transmission images associated to a production process for printed circuit board prior to said solder printing process; and inputting another X-ray transmission image of said substrate before said solder printing process obtained by said another inspection apparatus.

3. An inspection apparatus having an image generating device for generating X-ray transmission images for carrying out an inspection associated with a solder printing process, said solder printing process being one of a plurality of production processes carried out for producing component mounting substrates, said inspection apparatus being adapted to receive a substrate after said solder printing process, to generate an X-ray transmission image of said substrate by said image generating device, to input an earlier obtained X-ray transmission image of said substrate generated before said solder printing process was carried out on said substrate, and to use a differential image of said generated X-ray transmission image and said earlier obtained X-ray transmission image to inspect printed condition of said substrate; said inspection apparatus comprising:

registering means for registering setting data that are necessary for setting an inspection window to an area corresponding to each of lands in said differential image, conversion data necessary for converting density on said differential image to a value indicative of thickness of solder and a reference solder quantity at each inspection window before an inspection is carried out;

window setting means for setting a plurality of inspection windows to said differential image by using said setting data;

edge extracting means for extracting edges in each of said inspection windows;

mask image creating means for expanding said edges extracted by said edge extracting means and creating a mask image that sets density corresponding to an X-ray transmission image of a land at an expanded portion;

image correcting means for comparing said mask image with said differential image for each pixel and thereby obtaining a corrected differential image by correcting said differential image by replacing by zero the density of those of the pixels lower than that of corresponding pixel in said mask image and keeping unchanged the density of those of the pixels higher than that of corresponding pixel in said mask image;

solder quantity measuring means for converting the density of each pixel in each of said inspection windows of said corrected differential image, based on said registered conversion data, into a value indicative of thickness of solder and obtaining an integrated value as representing solder quantity;

judging means for comparing said solder quantity obtained by said solder quantity measuring means with said registered reference solder quantity for each of said inspection windows and thereby judging whether the quantity of solder printed on each of said lands is proper or not; and output means for outputting result of the judging by said judging means.

* * * * *